United States Patent [19]

Rosenfeld

[11] Patent Number: 4,932,416
[45] Date of Patent: Jun. 12, 1990

[54] METHOD FOR THE ANALYSIS, DISPLAY AND CLASSIFICATION OF EVENT RELATED POTENTIALS BY INTERPRETATION OF P3 RESPONSES

[76] Inventor: Joel P. Rosenfeld, 2526 Hartzell Ave., Evanston, Ill. 60201

[21] Appl. No.: 45,069

[22] Filed: May 1, 1987

[51] Int. Cl.$^5$ .............................................. A61B 5/04
[52] U.S. Cl. ..................................... 128/731; 128/745
[58] Field of Search .............................. 128/731–732, 128/733, 745–766

[56] References Cited

U.S. PATENT DOCUMENTS

| | | | |
|---|---|---|---|
| 2,944,542 | 7/1960 | Barnett et al. | 128/688 |
| 3,163,486 | 12/1964 | Tomes . | |
| 3,548,806 | 12/1970 | Fisher . | |
| 3,574,450 | 4/1971 | White et al. | 128/731 X |
| 3,893,450 | 7/1975 | Ertl | 128/731 |
| 3,971,034 | 7/1976 | Bell, Jr. et al. | 128/630 X |
| 4,188,956 | 2/1980 | John | 128/731 |
| 4,216,781 | 8/1980 | John | 128/731 |
| 4,331,160 | 5/1982 | Zito, Sr. . | |
| 4,493,327 | 1/1985 | Bergelson et al. | 128/731 |
| 4,579,125 | 4/1986 | Strobl et al. | 128/733 X |
| 4,610,259 | 9/1986 | Cohen et al. | 128/731 |
| 4,649,482 | 3/1987 | Raviv et al. | 128/731 X |
| 4,699,153 | 10/1987 | Shevrin et al. | 128/745 X |

OTHER PUBLICATIONS

Fischler, et al., *Neuropsychologica*, vol. 22, No. 5, pp. 559–568 (1984), "Brain Potentials During Sentence Verification: Late Negativity and Long–Term Memory Strength".
Fischler, et al., *Psychophysiology*, vol. 20, No. 4, pp. 400–409 (1983), "Brain Potentials Related to Stages of Sentence Verification".
Donchin, *Psychophysiology*, 18:493–513 (1981).
Fabiani, Karis and Donchin, *Psychophysiology*, 22:588–589 (1985).
Fabiani, Karis and Donchin, *Psycholphysiology*, 23:298–308 (1986).
Sutton S., et al. *Science*, 150:1187–1188 (1965).
Karis, D., et al, *Cognitive Psychology*, 16:177–216.

Neville, H., et al., *Proc. Nat. Ac. Sci. U.S.A.*, 79:2121–2123 (1982).
Pritchard, et al., *Psychophysiology*, vol. 23, No. 2, 166–172 (1986).
R. Johnson, Jr., *Annuals of the N.Y. Acad. of Sci.*, vol. 425 (1984) pp. 223–229.
Gomer, et al., *Physio. Psych.*, vol. 4(1) pp. 61–65 (1976).
Ford, et al., *Elect. Clin. Neuroph.*, 47:450–459 (1979).
Kramer, et al., *Psychophysiology*, vol. 23, No 1, 33–47 (1986).
Adam and Collins, *Elec. Clin. Neuroph.*, 44:147–156 (1978).
L. A. Geddes, et al., *Med. and Biol. Eng.*, vol. 13, No. 1, 89–96 (1975).
Kleinmutz, *Harvard Business Review*, Jul.–Aug. 1985, pp. 36–42.
Fischler, et al., *Neuropsychologia*, vol. 22, No. 5, 559–568 (1984).
Duncan–Johnson and Donchin, *Psychophysiology*, vol. 14, No. 5, 456–467 (1977). .
Nelville, et al., *J. Mem. and Lang.*, 25:75–92 (1986).
Kleinmuntz, et al., *American Psychologist*, vol. 39, No. 7, 766–776 (1984).
Saxe, et al., *American Psycholgist*, vol. 40, No. 3, 355–366 (1985).
Tueting, P, "Multidisciplinary Perspectives in Event-Related Brain Potential Research", U.S. Environmen- (List continued on next page.)

*Primary Examiner*—Angela D. Sykes
*Attorney, Agent, or Firm*—Olson & Hierl

[57] ABSTRACT

A method for recording and analyzing event-related potentials (ERP), and their respective P300 brain wave responses from a repeatedly presented guilty knowledge or control question stimulus interspersed with non-significant stimuli. A computer is utilized to interpret and analyze the responses for guilty knowledge and control question procedures.

5 Claims, 7 Drawing Sheets

OTHER PUBLICATIONS tal Protection Agency, EPA-60079-77-043 (1978), pp. 159-169, ed. David A. Otto.

Lykken, "The GSR in the Detection of Guilt", University of Minnesota.

Fishler, et al., "Effects of Sentence Forma and Content on Late Potentials During Sentence Verification", U. of Florida-Gainsville.

McCallum and Farmer, "The Effects on Brain Event-Related Potentials of Physical and Semantic Incongruities in Spoken Sentences", Burden Neurological Institute, Bristol, England.

Kurtas, "Event-Related Brain Potentials (ERPs) Eleicted During Rapid Serial Visual Presentation of Congruous and Incongruous Sentances", Department of Neurosciences, UCSD, La Jolla, CA.

FIG-2
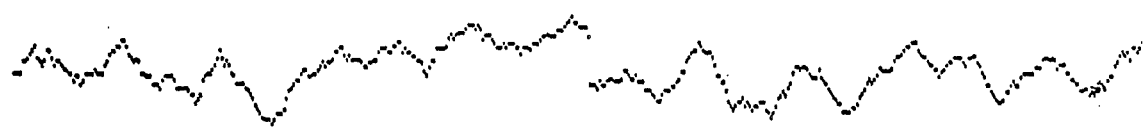
Ch/A
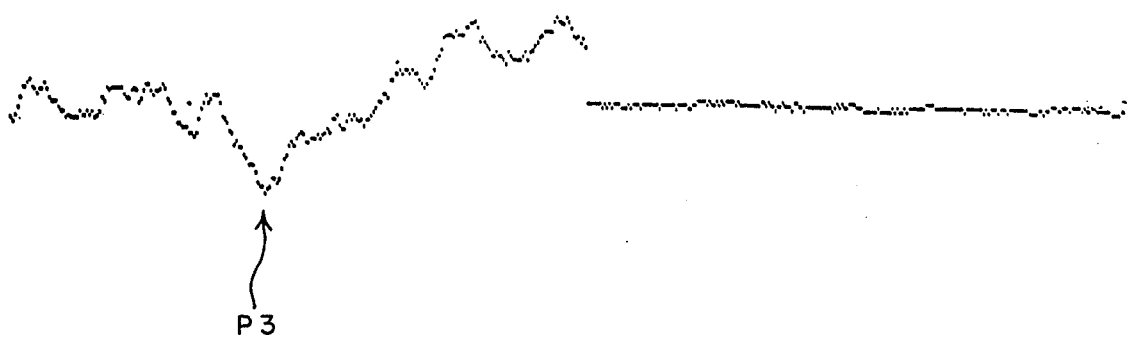
P3
NC/A
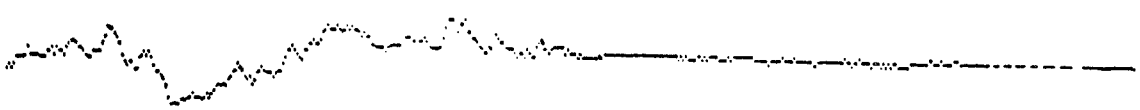

FIG_3
TBC/A
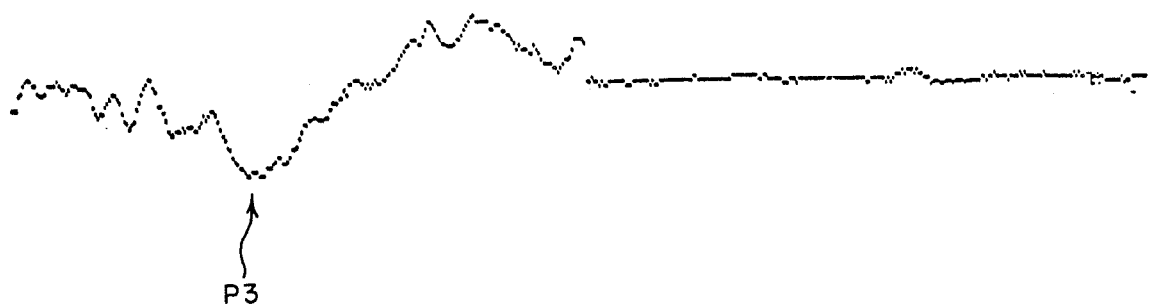
P3
NC/A

FIG-4
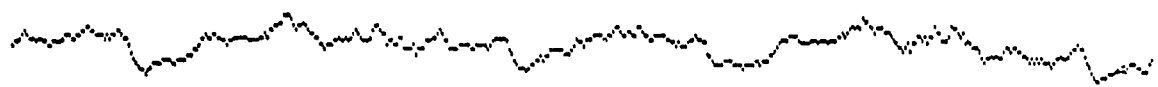
NC/A
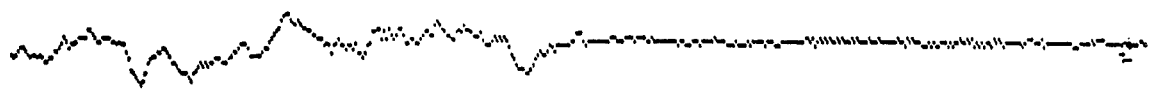
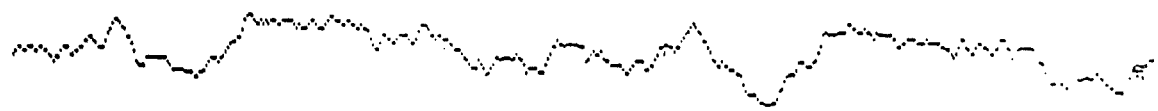
NC/A
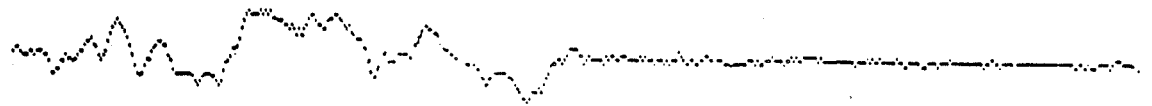

_FIG_5_
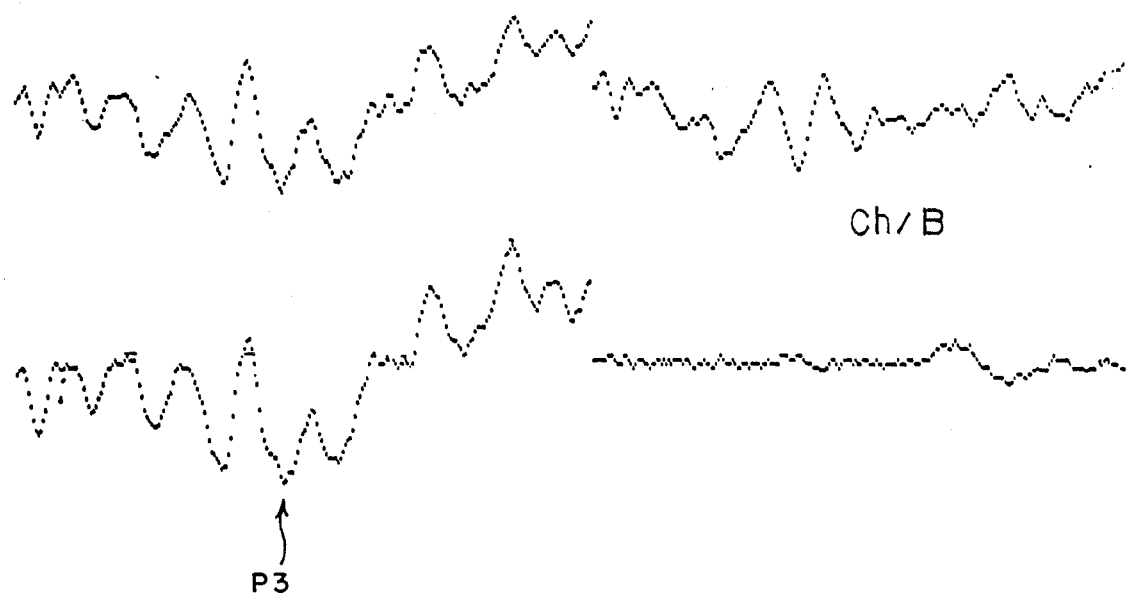
Ch/B
P3
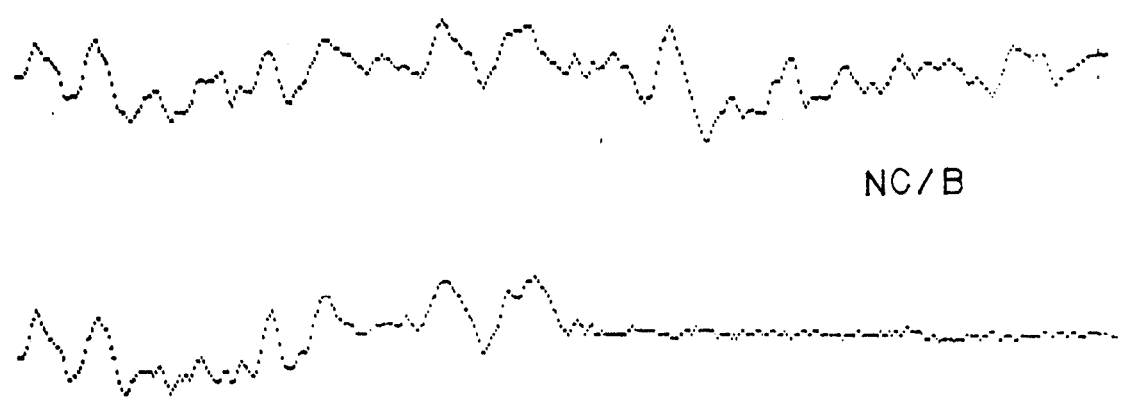
NC/B

FIG-6
TBC/B
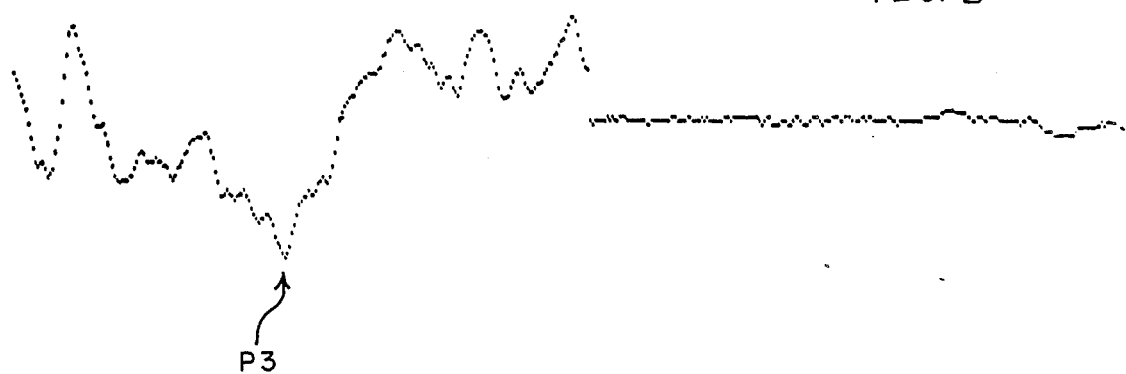
P3
NC/B
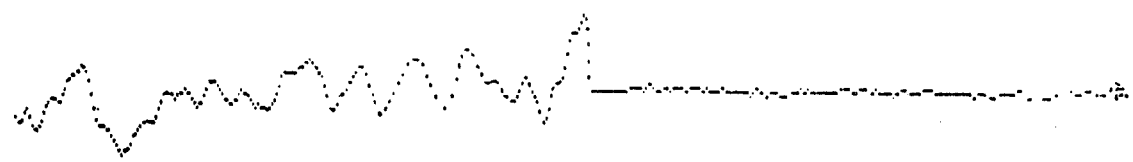

FIG_7
NC/B
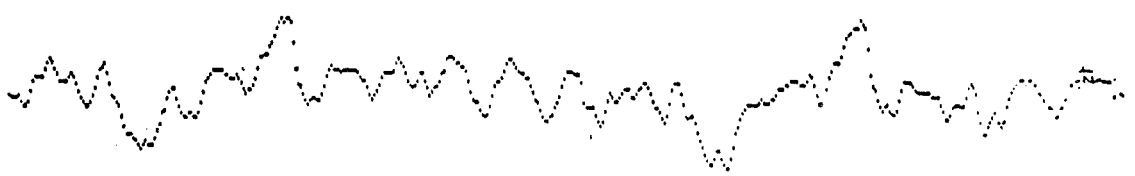
NC/B
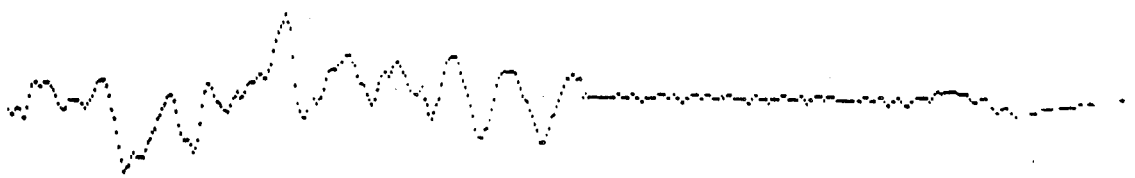

METHOD FOR THE ANALYSIS, DISPLAY AND CLASSIFICATION OF EVENT RELATED POTENTIALS BY INTERPRETATION OF P3 RESPONSES

BACKGROUND OF THE INVENTION

The present invention relates to a method for recording and analyzing event-related potentials (ERP), and more particularly to a method of measuring and determining P3 responses from a repeatedly presented stimulus or stimuli interspersed with non-significant stimuli and analyzing the measured ERP responses by means of a computer.

An electroencephalograph (EEG) is a device which measures and records brainwave activity by sensing spontaneous electrical potential of a person's scalp, cortex or cerebrum at various sites. Each EEG channel corresponds to a particular electrode combination attached to the patient. The sensed EEG potential at each channel is amplified by a differential amplifier, and the amplifier output signal is typically used to control movement of the recording pen of a polygraph. The EEG record is a long strip of polygraph paper containing a wave form for each EEG channel. The polygraph paper is driven at a pre-determined rate (e.g., 30 millimeters per second) and is graduated to represent predetermined time increments. A skilled neurologist must evaluate the EEG record to determine abnormalities in the EEG wave forms.

EEG signals exhibit different frequencies depending upon varying activity. The EEG signal frequencies are classified into four basic frequency bands, which are generally referred to as "Delta" (0–3.5 Hertz); "Theta" (4 to less than 8 Hertz); "Alpha" (8–13 Hertz); and "Beta" (greater than 13 Hertz). The neurologist determines the predominant frequency of a particular channel during a particular time period by measuring the period of the EEG signal wave form shown on the EEG record. This requires considerable training and is highly dependent upon the skill of the neurologist, since the EEG signal wave form typically includes multiple frequency components. EEG can be driven by specific extrinsic or endogenous events. For example, a regularly occurring stimulus will elicit a series of waves each time it is presented. The entire series is referred to as an event-related potential (ERP).

Besides the frequency of the EEG or ERP wave forms, the amplitude is often analyzed. Significance has been established when large amplitudes of brain waves occur at about 300 ms or more after the eliciting event. There is evidence to suggest that this P300 wave process is invoked when the updating, or "refreshing", of representations in working memory is required. Donchin, *Psychophysiology*, 18, 493–513 (1981); Fabiani, Karis, and Donchin, *Psychophysiology*, 22, 588–589 1985); and others. Large P300's are elicited by rare or unexpected events, when they are relevant to the task the subject is performing. Such events may lead to restructuring or updating of working memory, and this activity is part of the ongoing process of maintaining accurate schemas of the environment. The updating process may lead to an "activation" of the representation, or to the "marking" of some attribute of the event that was crucial in determining the updating process. This restructuring of the representation of an event is assumed to facilitate the subsequent recall of the event, by providing valuable retrieval cues, so that the greater the restructuring that follows an individual event, the higher the probability of later recalling that event. If P300 amplitude represents the degree of restructuring in working memory, then P300 amplitude should also predict later recall. Fabriani, Karis and Donchin, *Psychophysiology*, Vol. 23, 298–308 (1986).

In view of the current knowledge of the frequency and amplitude of brain wave forms and with the advent of widespread use of the computer in behavioral neuroscience, the analysis of data has become easier.

Oftentimes, it is desirable to have an objective method of determining whether or not a person has seen or otherwise has knowledge of a particular item, such as a weapon, a crime scene configuration, a secret document, a stolen object, or another person's face. Such knowledge is what is taught by prior art procedures and devices used in "guilty knowledge" tests, a sub-category of procedures used in physiological detection of deception ("lie detection"). The present invention is directed to a reliable, valid easy-to-use and accurate procedure for determining guilty or other knowledge on the part of an individual whose simple verbal report may be unreliable for various reasons.

If a discreet stimulus —a sound, a light flash, a tap—is presented to a human, his electroencephalogram shows a series of time-locked responses called event related potentials (ERP). It was shown in the 1960's that if a subject is presented with a series of stimuli of two types, e.g., a high tone and a low tone, and if either of those tones is presented in 20 of 100 trials (with the remaining 80 trials containing the other tone), the rare stimulus will evoke a large ERP referred to as "P3" or previously described P300 brain wave. In this so-called "oddball" paradigm, it is known that P3 amplitude varies with rarity. Sutton, S. et al., *Science*, 150, 1187–1188, (1965).

In the 1970's and thereafter, other workers reported that P3 is evoked by words (or pictures) previously seen by a subject when presented in a word (or picture) series which also includes novel words (or pictures) which fail to evoke P3. Karis, D. et al., *Cognitive Psychology* 16, 177–216; Neville, H. et al., *Proc. Nat. Ac. Sci. U.S.A.*, 79, 2121–2123, (1982).

The present invention relates to a novel method which utilizes both the aforementioned effects so that one can tell by ERP inspection alone, which of the presented stimuli has previously been seen by the subject. The invention further relates to an apparatus which provides means for a repeated presentation of the significant stimulus and means for analyzing the ERP responses to determine significant P3 responses.

Sutton supra used P3 responses in an "odd-ball" procedure with simple auditory stimuli, e.g. high tones and low tones, that were presented singly to subjects and whatever tone was presented less often evoked a P3 reponse. Pritchard, et al., *Psychophysiology*, Vol. 23, No. 2, 166–172 (1986) utilizes the "odd-ball" paradigm in which the stimuli is a simple visual flash differing in brightness. Johnson, Jr. *Annuals of the N.Y. Acad. of Sci.*, Vol. 425, pages 223–230 (1984), like Pritchard, discuss studies utilizing P3 responses relating to memory updating processes, expectancy processes, surprise, and so forth. None of the prior art articles disclose the odd-ball procedure with repeated, meaningful word stimuli in the context to be utilized to detect guilty knowledge or other recognition processes. Fabiani, et al. *Psychophysiology*, Vol. 23, pp. 298–308 (1986) and Neville, et al. supra utilize verbal, meaningful stimuli in a variant kind of "odd-ball", paradigm bearing on recognition memory, however, but differ greatly from the present invention by two aspects: (1) these studies were not and could not be configured as field-relevant deception detection paradigms, because (2) both novel and previously seen words (or pictures) in these studies were never repeated within the EEG run. The average ERP to previously seen words (or pictures) was an average of responses to a series of all different words (or pictures); the average ERP to novel words (or pictures) was likewise an average of responses to all different novel words (or pictures) This kind of paradigm is likely to be specifically unsuited to real criminal-type investigations since it is usually a single item (the murder weapon, the stolen item, the classified document), which is involved in a real crime. The Fabiani and Neville reports are directed at and tailored to scientific elucidation of memory processes. In these studies, the repetition of words is avoided for fear of engaging habituation processes which would tend to reduce P3 effects.

In the present invention, the "odd-ball" item is "odd-ball" by virtue of its familiarity (e.g., as guilty knowledge). The stimuli are all meaningful words, and they are presented in the simplest possible, basic "odd-ball" design.

There are other studies in the literature which do not use quasi verbal stimuli which are repeatedly presented. A review of the literature reveals that these studies are not using "odd-ball" paradigms, and are, in fact, studying memory processes with extremely complicated procedures tailored to these purposes: For example, Gomer et al., *Physio. Psych.*, Vol. 4 (1) pp. 61-65 (1976), (1976), Ford, et al., *Elect. Clin. Neuroph.*, 47:450-459 (1979), Kramer et al. *Psychophysiology, Vol.* 23 No. 1, 33-47 (1986) and Adam and Collins, *Elec. Clin. Neuroph.*, 44:147-156 (1978). All use "go-no go" or pattern matching paradigms. A set of letters or numbers is memorized and then the subject is given a trial series in which he decides whether ("go") or not ("no go") a memorized target stimulus is presented. There are typically other differences between these procedures and the present invention: The present invention requires but one series of trials; others use several sets. The present invention requires no feed-back whereas the prior art methods do. The prior art methods use warning tones whereas the present invention does not. It is notable that typically, the prior art reports P3 responses to both target and non-target stimuli. Although target effects are often reported to be bigger, unambiguous use of P3 responses in field investigations of deception requires the kind of virtually all-or-none results that are seen in the present invention. Further, the prior art studies use simple stimuli, digits or letters, rather than meaningful words. The intent of the prior art methods was the elucidation of memory retrieval processes and are more often interested in P3 latency than in amplitude.

Instruments have been used to determine psychological stress, for example, the apparatus described in U.S. 2,944,542 relates to a blood pressure measuring device that indicates variations in the velocity of pulse waves, thereby indicating a change in emotional state. U.S. 3,971,034 describes a method and apparatus for identifying psychological stress by converting oral impulses into electrical signals and recording, observing and analyzing those signals. U.S. 3,893,450 relates to a method and apparatus for examining brain wave form by providing stimuli such as light and determining the characteristic of a mathematically determinal point in the brain wave forms of the subject. U.S. 4,188,956 relates to a method of acquiring compressing and analyzing neurometric test data by means of a digital computer base system. U.S. 4,579,125 relates to a method for processing analog EEG signals to provide an indication of cerebral activity. None of the teachings of these references however, have been used for the combination of a method to determine P3 responses from a repeatedly presented stimulus interspersed with non-significant stimuli to obtain results directed towards lie detection and control question testing.

SUMMARY OF THE INVENTION

In accordance with the present invention, a method of measuring and determining P3 responses from a repeatedly presented stimulus or stimuli interspersed with non-significant stimuli and analyzing the measured ERP responses by means of a computer is described. The method comprises presenting to a subject stimuli that are usually rare and relevant interspersed in a series of frequent and usually irrelevant stimuli, recording the reaction to the irrelevant stimuli by P300 brain wave forms and interpreting the amplitudes of those brain waves which form within a certain time segment post-stimulus to indicate "knowledge". The interpretation and analysis of the brain waves is performed by computer in the context of the present procedure. Guilty knowledge and control question tests may be utilized for various purposes.

BRIEF DESCRIPTION OF THE DRAWINGS

FIGS. 2 through 7 graphically represent P300 brain waves.

DETAILED DESCRIPTION OF THE INVENTION

Figure 1:
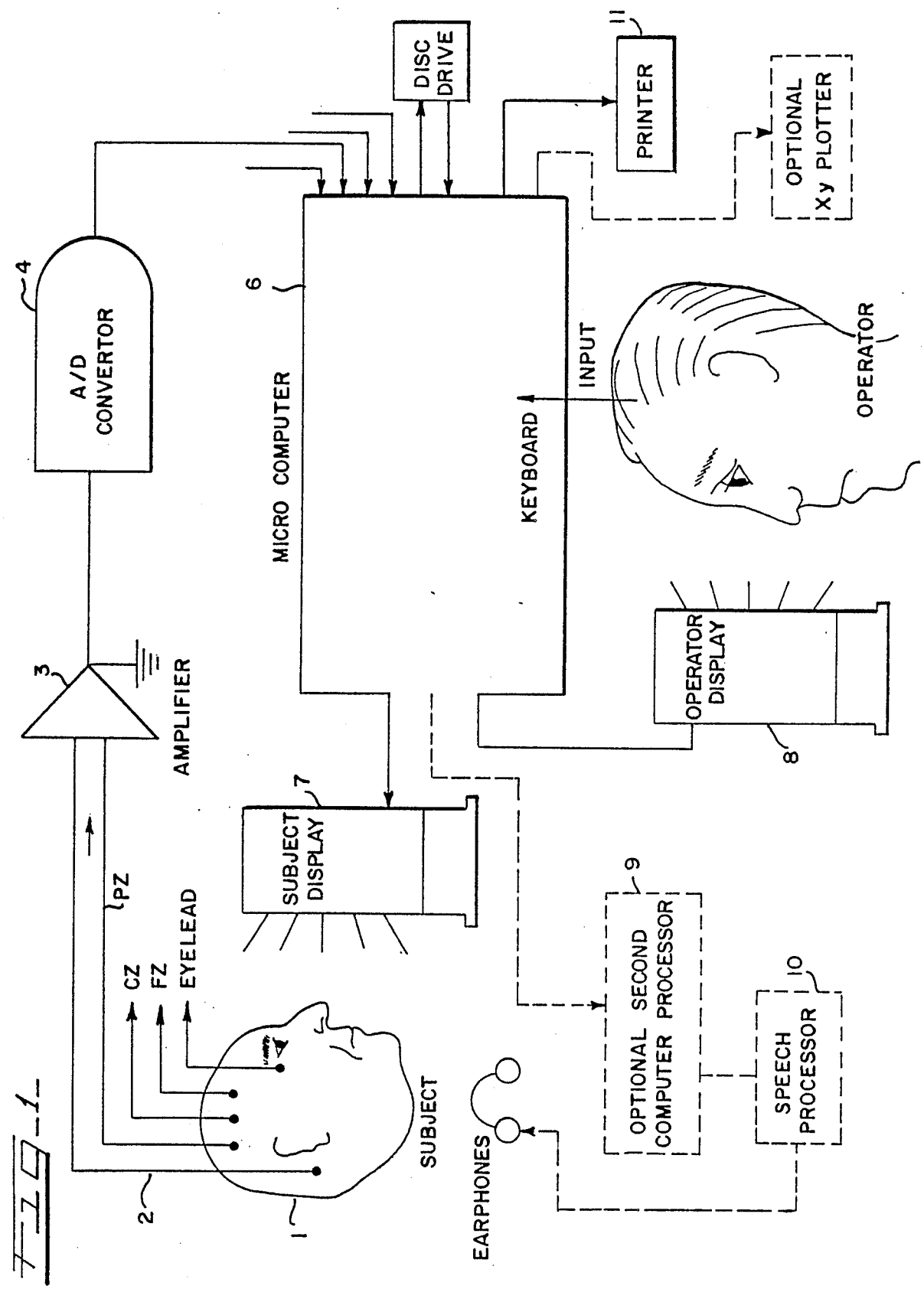
FIG. 1 is a schematic representation of the system utilized in the present invention for P300 analysis.

The present invention relates to a method and apparatus for recording and analyzing event related potentials (ERP) and specifically a method of measuring and determining P3 responses from a repeatedly presented stimulus interspersed with non-significant stimuli and analyzing the measured ERP responses by means of a computer. The present invention provides a method for analysis and display of quantitative features extracted from event related potentials generated by the brain in response to presented conditions and challenges. While many embodiments of the present invention are known and recognized by those skilled in the art, the present invention is directed at controlled testing methods, i.e., guilty knowledge detection or control questioning. This emphasis is not intended to be limiting.

Accordingly, the method of the present invention relates to evoking event related potentials, interpreting and displaying the P300 responses which comprises attaching a series of electrodes to the subject scalp, presenting a specified challenge or condition relating to guilty knowledge or control questioning, recording the electrical brain activity relating to the cognitive processes, extracting significant quantitative features from those data, particularly the amplitude of P300 brain waves, and statistically analyzing the extracted features according to a systematic procedure. P300 brain wave amplitude ranging from 400 to 800 millisecond post-stimulus is determined to be interpretive of a significant response in the controlled testing methods of the present invention, preferably either in guilty knowledge detection or control questioning.

GUILTY KNOWLEDGE DETECTION

With reference to FIG. 1, a subject is seated before a computer terminal with electrodes attached to three scalp sites: the vertex (CZ), central-parietal (PZ) and central-frontal (FZ). Optionally, earphones are also worn. Event related potentials (ERP) are amplified 60,000 times and filtered to exclude activity below 0.1 and above 30 Hz. Eye movement is recorded with electrodes above and below the eyes and processed for disqualifying purposes. Eye movements and blinks can produce artifacts which must be removed from the data base. At the conclusion of a recording, average wave forms from CZ, PZ, and FZ and from the eye channel are available. The flatness of the wave forms from the eye channel insures artifact free testing. Further, muscular activity from the jaw and forehead surfaces can be measured and utilized as normative criteria for rejection of data contaminated by abnormal muscular activity. This is particularly more important for field applications in which subjects motivated to defeat the test can clench jaws and thereby generate muscular activity signals which would be noise sources for ERP data.

The following procedures below can be utilized in a guilty knowledge paradigm and/or are adapted to auditory presentation and stimuli in accordance with the schematic representation of FIG. 1. The procedures are shown in both laboratory setting and a field setting.

| | Procedures with Subjects | |
|---|---|---|
| | Lab | Field |
| 1. | Guilty knowledge induction: Subject chooses an item from a box. Experimenter is not told what item is chosen. Subject is asked to pretend he has stolen his chosen item and is taking a lie detector test. | (e.g.) Criminal steals an item |
| 2. | Instructions to subject, pre-prime phase: Briefly, subject will be shortly viewing 9-word set "P", which does not include his chosen/stolen item. He is now told to count the word "Rubies" which will appear. He is also told he will not be able to help noticing when his chosen-stolen item appears. In fact, in phase #3, the next (priming) phase, he will see nine words presented one at a time every 2 seconds. The word "rubies" will appear, but the chosen/stolen item will not appear. The aim is to raise expectancy and anticipation. Warnings about failing to pay attention are given. Subject is warned that he must have a reasonably accurate count of counted item or we'll know of inattention. He's also told he will not be able to help noticing chosen item when it is given. | Subject likewise will be told to watch for an item he is suspected of recently stealing. The item is not named. He is told to look for and count one word in the set. It can be arbitrarily selected (as at left) or actually be an item he has stolen at a different time as determined by records and/or interrogation. It is not the item he is currently suspected of stealing. Warnings given as at left, about paying attention. |
| 3. | Prime Phase Subject views words from set "P". These are all different from but comparable in value, size, etc., to the items of set "E" with which he will be later presented in the Test run. He has been told to watch for one item ("rubies") to count. 108 trials in all are used. Word choice is randomly determined, and each word is presented about 12 times each. | Similarly |
| 4. | Reinforcement of Awareness of Guilty Knowledge Experimenter/operator asks subject for count of counted item and if he saw chosen/stolen item. When subject says "no" the experimenter asks "Do you recall chosen item?" When subject replies affirmatively, experimenter tells him to write | Operator asks for count of counted word. If it is off by 3%, suspect is warned he is suspected of non-cooperation. He is asked if he saw a recently stolen item during the stimulus |

| Procedures with Subjects | |
|---|---|
| Lab | Field |
| a 100-200 word essay explaining choice. This is privately done and the essay paper is still retained by the subject who has no reason to believe that experimenter knows identity of actually chosen item. | presentation.<br><br>Suspect is interrogated so if he's guilty this procedure will reinforce his knowledge and memory of stolen item, though it is not mentioned. He can also be asked to think hard about any recent crimes. |
| 5. Pre-Test Phase Instructions | |
| Subject is instructed as in phase 2 except that "diamonds" is the to-be-counted word. Attentional warnings are given again. | Similarly. |
| 6. Test Phase | |
| Subject views word set "E" whose contents are different than "P". 9 words are used and this time, the chosen/stolen item is one of the 9 words repeatedly presented. 108 trials are given as in 3. Another embodiment of this procedure can be utilized where instead of the chosen word's being randomly presented about 12 times, it is presented on trials 20, 26, 30, 50, 53, 60, 81, 87, 90, 99, 102 and 108. The aim of this is to make its presentation appear more rare. The priming procedure is designed to raise anticipation; Much time passes (in Phase 3) and the chosen item is optimally rare; i.e., it is absent. Then 19 trials go by in this test phase before it finally appears for the first time on trial 20. Since the P3 response of brain is in response to a rare ("odd-ball") event, these procedures are calculated to heighten this effect. | As at left, except actually stolen item of which suspect is suspected of stealing is is presented along with 8 other words. |
| 7. Post-Test Validations | |
| Subject is asked to write down all recalled words (from set "E"). He has 5 minutes; (5-6 items normative.) He is then given recognition test where the words he failed to recall in recall test are presented in multiple choice fashion for him to identify. Total recognition is normative. Count of counted item is taken. | Similarly. If recall and recognition are sub-normative, and/or if count of counted item is >3% off, suspect is warned of possible report of non-cooperation. Another test may now be given; i.e., all procedures to be repeated on another day. |
| 8. Standard P3 Test (optional) | |
| Subject is given standard P3-odd-ball paradigm with rare and frequent simple verbal stimuli to validate normal presence of P3 response to rare, counted stimuli. This is as recommended by Fabiani et al. (1987). | Similarly. |

FIGS. 2 through 7 show data from randomly selected subjects who ran the foregoing test and were not eliminated for non-cooperation, e.g., poor memory test results, excessive artifact, etc. Two sets of four (4-set) waves (average ERP's voltage as a function of time) are shown on each page for subjects A and B. In the set of four waves, top left is CZ, top right FZ, bottom left, PZ and bottom right is the eye movement average which should be flat. Each trace is labeled with letters to the left and right of a slash. To the right is the subject identification; to the left is an item type which elicited the wave set. That is, "CH/A" refers to the chosen item for subject A, "NC/A" is a non-chosen; non-TBC item for subject A; "TBC/A" is the to-be-counted response 4-set for subject A; P3 responses are indicated with arrows. To the eye, they seem to appear only in the CH and TBC waves. Positivity is down, vertically, one CM=10 uV sweep length =1280 m sec. Stimulus is not presented until 100 m sec. into the sweep (about a centimeter, horizontally).

The average EEG amplitude for 100 m sec. prestimulus is the base line from which the dependent values are subtracted. Those values are: 1. average value from 400 m sec. to 800 m sec. post-stimulus; 2. maximum amplitude of 100 m sec. segment between 400 and 800 m sec. An auxiliary reference for these P3 estimates is the maximum negative peak immediately following P3, e.g., from 700 to 1400 m sec. If the chosen/stolen item values are significantly larger than corresponding values for all other items (except for counted item), this subject is presumed to have guilty knowledge. It is evident that all ERP's to chosen-"stolen" and to TBC items show P3's especially in the PZ electrode. The ERP's to other ("NC") items do not show ERP's. Accordingly, it should be emphasized that what is pointed out as a P3 is in each case confirmed by computer analysis. Comparison should be made from CZ record of one 4-set (EG "CH") to the CZ record of another 4-set (EG "NC"), from FC to FC and from PZ to PZ, etc. The bottom left in each 4-set should be compared with bottom left in a comparison 4-set. Waves must be compared at matching time segments.

The criterion for a diagnosis of deception, that is, that the chosen or stolen item's ERP values are larger than all other comparable ERP values is extremely conservative and could lead to occasional innocent diagnoses of guilty persons. Norms may be developed according to the desires of the investigator, for example norms that may be developed for a different, less-conservative but valid criterion are as follows: the average of all novel (non-chosen/stolen, and non-counted) items are calculated. This mean is subtracted from the mean of the ERP associated with the chosen/stolen item. The difference obtained is either improbably large and indicative of deception, or it is not sufficiently large. Exact values for decision criteria will come from a normative study of 100 normals in which the properties of the distribution of differences (chosen/stolen values versus mean of other item values) are obtained in a situation where a control word is used in place of the subject chose/stolen item. In test runs, difference values more than 2 standard deviations from the mean have only a 2.5% likelihood of being obtained by chance. Of course, 3 or more standard deviation criterion may be utilized.

CONTROL QUESTION TEST

In the previously described paradigm, it is assumed that only a guilty person has specific guilty knowledge which his brain will recognize. Prior to the actual lie detection test, it is assumed he does not know that the investigators have a specific piece of guilty knowledge about the crime which they will test him with, e.g., the specific item stolen, etc. It is assumed that there has been no publicity or interrogation about this detail prior to the test. If the individual has in fact been interrogated about a particular item of knowledge, then whether one uses standard autonomic response polygraphy or the method of the present invention, a response to the test item may not be due to guilty knowledge but to the priming effect of interrogation about the item. An innocent individual questioned about a stolen necklace could respond to the test item "necklace" simply because he knows he is suspected of stealing the necklace in consequence of his having been questioned about it. Possibly, he has heard of the specific details of a crime which were publicized, prior to interrogation. Interrogation itself will then impart an oddball quality to the item; i.e., it may have been the only one he has been questioned about. In this regard, the guilty knowledge procedure may not be useable. Further, in some crimes, the circumstances are such that the actual perpetrators do not know the specific details of a crime for various reasons, such as anxiety, etc. In these situations, the guilty knowledge test may be of limited use.

Control question procedures have been developed for these types of situations. In prior art control question procedures in autonomic response polygraphy, during the suspect's questioning about the matter under investigation, he is also intensely interrogated about other acts in crimes or faults, stated to be pertinent to the matter under investigation, including the minor ones of normal childhood. Information regarding thought about but not actually perpetrated acts may be elicited. The so-called "control questions" are formulated by the examiner which will ask these general areas which are not actually specific to the crime under investigation. The suspect, however, is told that during the actual lie detector test, investigators will be interested in physiological responses to all questions (i.e., in the specific crime relevant as well as in control question areas). The investigators, however, are actually interested in responses to specific crime relevant questions The suspect is told this on the theory that if he is innocent he will be just as upset and responsive about control area questions as he is about crime relevant areas. The guilty person, however, knows he is guilty of a specific crime and is suspected to be more concerned about it than about control areas since his own detection apprehension regarding his crime stires up his concern His autonomic nervous system is expected to respond more to relevant than to control questions.

Although the autonomic responses in the standard control question test are usually thought of indexing differential general sympathetic arousal and emotionality levels, it can be argued that the specific information contents of control and relevant questions are also differentially responded to in the control question test Accordingly, it is further surmised that ERP responses of brain are more likely to differentiate information differences than are integrated physiological measurements as in prior control question test procedures. This follows from the fact that the brain's response to input information must temporarily precede and indeed direct the autonomic response output indexing emotion Additionally, this emotional state is likely more subject various ongoing "noise" sources, such as that due to being under suspicion, than is the cognitive state, the subject's knowledge of his guilt or innocence. This knowledge should remain largely independent of background emotional level, i.e., whether or not one is upset or placid, one knows whether or not one is innocent or guilty. Accordingly, the method and apparatus of the present invention measure P3 responses in a control question procedure.

In the control question procedure, which is one of many embodiments of the present invention, that follows, electrophysiological and data analytic methods are the same as those described in the guilty knowledge procedure. Similarly, subjects in a lab situation choose one item from nine in a box. The one of nine ratio makes a relevant item have an 11% probability. Since P3 is evoked by rare (less than or equal to stimuli, the relevant item probability is less than 20%.

In this procedure, differing from the guilty knowledge test procedure, the subject will be asked to identify an act he is guilty of from among a context of other acts including innoculous acts such as "had a birthday", etc. as well as acts regarding general (control question) areas such as "stolen from work". The control question items are, as in the prior art control questions procedures, designed to involve and arouse innocent subjects. The purpose of the innocuous item (as with the irrelevant questions also used in prior art) is to establish a base line response level.

| | Lab | Field |
|---|---|---|
| 1. | Crime occurs | |
| | Subject chooses an item, e.g., a camera, from a box of 9 items in response to question "choose an item you'd like to keep if you could." He will later be asked to pretent he stole the item. | Suspect commits crime, e.g., he steals a camera from his place of employment. |
| 2. | Criminal and control area interrogation | |
| | (a) Lab "guilty" - Subject is told that among the several subjects who are in the lab that day, one selected a camera (a lab "innocent" subject is questioned about an item he did not choose) and the investigators must, after various procedures, decide who it is who chose the camera. Various questions are asked about the subject's possible interest in cameras. This procedure is supposed to model the criminal investigation. | (a) Suspect is interrogated in this real investigation, about the crime but also — |
| | (b) Subject is then asked in detail about other crimes planned, thought about, wished, or done in near and distant past. This is meant to stir up concern about the control question area in "innocent" subjects, but obviously, "guilty" subjects must be treated similarly since guilt and innocence are not known a priori in field situations. | (b) in a control area so as to arouse an innocent subject's concern with control items; to equalize concern across control and relevant items. |
| 4. | Priming Phase | |
| | (a) Subject's electrodes are attached and he is told he will see (or hear in an auditory embodiment) a series of phrases which describe various acts, thefts and crimes and which may, include the phrase "stole the 'item'", where 'item' will correspond to the stolen/ selected item in phase 1, above. Subject is also told he'll see (hear) the phrase "came to lab" on occasion. When he sees this choice, he is told to press the button in his dominant hand (right if right-handed) to signify "yes, this is true." Subject is then told to press button in non-dominant hand so as to say "no" to other items if they are not true. In lab condition, subjects are told that this means they must lie in order to evade detection. The purpose of the button-press choices (with one built-in "yes" response) is, as before, to force attention to and a decision about the stimulus on each trial. In this priming phase, subjects see a set of phrases different from what they will see in the actual test run(below). There are some similarities, however, in context. E.g., if they are to see (hear) "cheated the boss" in this priming phase. If they are to see (hear) "took the camera" in the test run, they will see (hear) something like "took the telescope" in this priming phase. They never do see the chosen/stolen item in this priming phase. As in the GK test, this priming phase is designed to raise anticipation for the actually relevant act (e.g., "took the camera") and to make it appear as a more dramatic rare event when it appears later during the test run. For innocent subjects, these questions are also a kind of priming control questions and are designed to raise concern about other areas of suspected crime and dilute the oddball quality-generating effect of being suspected of the relevant crime. | (a) these procedures are quite parallel to the procedures at left except as noted. It is also noted that these priming procedures are not utilized in prior art lie detection. There is no need to stir up expectancy and rareness with autonomic response polygraphy. There is with P3 methodology. |
| | (b) Subject is subjected to 108 priming stimulus presentations (9 phrases, 12 times each). | |
| | (c) Subject in lab model is asked "did you see (hear) your 'crime'" to which he will say "no". He is then asked to write an essay about his chosen item. (This is for lab model only so as to reinforce subject's knowledge of his choice.) | |
| | (d) Subject is told "We believe, based on your reaction times on your button presses and on the brain waves we've seen so far that you really have at least thought about stealing in the past, that you may have been involved in minor crimes in the past and in cheating or fooling people for your own gain. In this last test to come next we'll identify your present crime." | |
| | (e) In the lab situation we would also add "we know you took either the camera, the ring, or the pearls and this last test will tell us." A "guilty" subject (who did choose camera should react to "took the camera" in the next test. A lab subject manipulated to be "innocent" will have chosen a different item, either ring or pearls (in this example) and should not react to "took the camera" but to a control item such as "took the pearls". | It may be possible to use a procedure like this in the field also. (See 5b, below.) |
| 5. | Test Run Phase | |
| | (a) After being instructed to press the "yes" button if he sees a true answer such as "took lie test" he receives the following stimulus presentations 12 times each: one relevant item: "took the camera", 3 general control items: "stole from work", "think of stealing", and "try to steal", 3 irrelevant items to which the subject must respond "no" truthfully: "born a man" (if a woman), "went to college" (if he did not go), and "had small pox" (if didn't); and finally a truthful irrelevant item "took lie test" which must be answered "yes". Lab "guilty" | |

| Lab | Field |
|---|---|
| subjects are again instructed to lie if they see their "crime". (b) In the lab situation, one or more of the control items may be replaced by more specific control items such as "took the pearls". An experimentally manipulated "innocent" subject will have actually taken (chosen) the "pearls"but will have been questioned about "camera" as in 2a) above. A "guilty" subject will have taken and will have been "interrograted" about "camera". He will also have been interrogated about a non-chosen item to match the "innocent" subject's treatment, but he knows what his true "crime" was. It is noted that the irrelevant "no" items here are a significant variation from what is presently done with control items in standard autonomic response polygraphy in which the irrelevant items are typically answered (truthfully) "yes". We have subjects say "no" truthfully to these items so as to preserve the uniqueness (oddballness) of the truthfully answered, "yes"-irrelevant item. We do not want big P3 responses except to the target and relevant items in guilty subjects and to target and control items in innocent subjects. Thus we want to minimize uniqueness of items not designed to elicit P3 by making behavioural responses to them the same. Only the relevant and control items (for guilty and innocent subjects, respectively) will be unique (along with the "yes" irrelevant item) in that the subjects will be concerned about their "no" answers to them. | This replacement of control questions can be done in field also if suspect can be reasonably persuaded that he is under suspicion for having stolen other fictitiously missing items. In this case a modified version of procedure 4e) above can also be used in priming phase. |

The ERP data are treated as previously described in the guilty knowledge procedure. Subjects are diagnosed as innocent if the P3 responses to control items are larger than those to relevant items. The judgment is reversed if the P3 to relevant items is larger.

APPARATUS

Referring to FIG. 1, there is shown the system according to the present invention for analyzing the cognitive process of recognition comprising a subject 1, with electrodes 2 attached thereto to pick up cortical EEG activity from the scalp and bring it to biological amplifiers 3. In the schematic representation, only one complete EEG channel is shown. In practice, there are two other channels and an eye channel present. Therefore, there are 4 amplifiers and A/D converters, represented here by numeral 4. Amplifier 3 receives brain waves from the head of the subject by way of electrodes 2. The electrodes 2 are placed at the vertex, central parietal and central frontal portions of the subject's scalp. An EEG cap (i.e., as manufactured by Electrocap, Inc., Dallas, Tex.) of molded pliable rubber may be used in which disposable electrodes can be placed to make contact with the scalp. The P3 activity of the brain can be detected by the electrodes. The EEG amplifier 3 amplifies the electrical signals from the brain by a factor of approximately 60,000 which makes it resolvable into at least 50 computer units by the A/D converter 4 in the next stage, but does not amplify the activity to a level high enough to overdrive the A/D converter. Any conventional converter may by utilized, and the following description does not intend to be limiting. The A/D converter is an 8 bit unit with $2^8 = 256$ possible values (0–255).

The 8-bit main microcomputer 6 has several functions.

1. After the main program is loaded from floppy disk, the computer receives information from the operator concerning biographical information about the subject. It also receives information from the operator concerning which questions will be put to the subject, how many trials are to be run, what intertrial interval ($I_t$) to use, and other parametric information.

2. It then presents the question-items to the subject every $I_t$ seconds through display terminal 7. It accomplishes this either by sending item word characters simultaneously to the subject and operator display terminals 8 or by sending a code number (via an interface) to the optional second microcomputer 9. This unit causes a speech processor 10 to output the question items in spoken form to earphones or a A/D channels for the operator's inspection.

At a precise time (100 m sec or 300 m sec for visually and acoustically presented items, respectively) prior to item presentation, the main computer repeatedly samples all 4 A/D input channels once every 5 (visual) or 8 (acoustic) m sec, 256 times. Each sample is sent to 2 (optionally 3) places: (i) a temporary memory buffer of 256 memory byte locations per A/D channel, (ii) a permanent, accumulating sum memory buffer of 512 bytes per a/d channel (and optionally (iii), the optional second computer processor's memory). The functions of these storages are: (i) the 4 temporary buffers will be scanned for artifacts. Eye and ERP channels are inspected. If an artifact is found, all channels' temporary storage values are subtracted from their respective accumulating sum buffers. The temporary buffer is erased on every trial as the new temporary data are stored ("destructively") on top and in place of the old values. (ii) The accumulating sum buffers add each trial's data into an accumulating double precision (i.e., 16 bit) sum. There are 36 of these 512 byte buffers; 4 channels ×9 different items. The main computer determines on each trial which of the 9 question-items was presented, and thus, which of the 9 sets of 4 channels the trial's data go to. At the conclusion of the run, each of the 36 accumulated sums is divided by the numbers of trials having contributed to it to yield the 36 average wave forms. This is accomplished by a second program which performs other post-run analyses as described below. It is automatically entered from disc at the end of the main program. (iii) The optional second microcomputer processor, besides being used, as noted above, to drive the speech unit, stores each single trial's complete data set. This storage is of all unprocessed single trials'single sweeps. The eye channel data is stored but not necessary for analysis. This ERP data is stored so as to enable performance of a varimax-rotated principal component analysis mostly for research purposes after the main run. Two separate second processors may be utilized; one to store the 432 sweeps and one to handle speech synthesis.)

The printer 11 outputs 3 kinds of data: (i) It echoes all the operator-entered parameters from prior to the run. (ii) It outputs the numerical results of the wave analysis softwave, e.g., latency and amplitude values of P3 in the averaged ERP's determined. It also outputs in the guilty knowledge test the results of comparing (subtracting) guilty item-evoked ERP's with control item-evoked ERP's. In the control question test it outputs the results of comparison of control and relevant items, i.e., the printer prints diagnoses of guilt or innocence or non-cooperation, or indeterminateness. (iii) The printer also "draws" all 36 averages on paper for confirmation and further study. An optional XY plotter plots the waves.

FUNCTIONAL DESCRIPTION OF SOFTWARE FOR WAVE ANALYSIS AND INTERPRETATION

(a) Preliminary collection of average ERP's

As described in the hardware description, the main computer program accumulates all artifact-free single waves for a given electrode site (e.g., PZ) evoked by item #1 into a summated ERP (for PZ) number $1-E_{p1}$. Likewise it collects $E_{p2}, E_{p3} \ldots E_{p9}$. It does the same for the CZ and FZ sites, to yield $E_{c1}, E_{c2} \ldots E_{c9}, E_{f1}, E_{f2} \ldots E_{f9}$. There are thus 9 (items)×3 (sites)=27 sums. The eye movement channel also yields 9 sums.

(b) Analysis and Interpretation

After the last trial, the main program calls in another program which divides all sums by the number of contributing trials to yield the averaged ERP for each item for each site. An averaged ERP is a waveform showing voltage as a function of time, as is the single ERP, except that the voltage for each sequential time point in the average ERP is the average voltage of the ERP at that time point. Using 5 m sec per time point resolution as accomplished with visual presentation, $E_{p1}$, time point #1, is the averaged ERP voltage over all item #1 trials obtained by averaging all item #1 trials' samples of voltage taken 5 m sec into the recording epoch; time point #2 is the averaged ERP voltage over all item #1 trials' samples of voltage taken 10 m sec after recording start, and so on.

For each average ERP the program now calculates the average value of the first 20 time points (which=100 m sec at 5 m sec/time point). This is the pre-stimulus baseline EEG level, since recording begins 100 m sec prior to item onset in visual presentation (and later for acoustic presentation). Next, for each sequential 100 m sec segment between 400 and 700 m sec post stimulus (=500 to 800 m sec from recording onset), the program calculates the average voltage. Thus it has the average from 400 to 499 m sec, from 401 to 500 m sec, from 402 to 501 m sec . . . and so on to 601 to 700 m sec. Each averaged segment value is now subtracted from the prestimulus baseline segment value. The program retains the maximum (peak) value among these sequential segments and defines it as the P3 value for the average. P3 is ordinarily found between 400 and 700 m sec post stimulus when complex verbal stimuli are used. Its peak latency varies but it ordinarily falls somewhere between 400 and 700 m sec. P3 is thus defined as the maximum positive voltage average (of 100 m sec of data), referenced to baseline, between 400 and 700 m sec post stimulus for each wave. This is the main measure and the program prints it as "MX" and also prints its latency ("LX") corresponding to the midpoint time point of the chosen MX segment. This is done for all 27 averaged ERP's.

An auxiliary direct P3 index is accurately diagnostic; it is called "DX". To obtain DX the program computes the minimum value of sequential 100 m sec segments between 600 and 1200 m sec post-stimulus, referenced to baseline. This is called "NM" and is also referenced to baseline. DX, then, =MX−NM. The program also causes the printout of NM (and its latency, LM) and DX. NM is the maximum negativity (minimal value of ERP) between 600 and 1200 m sec post-stimulus. It corresponds to a final negative component; N5, which is typically seen when the amplifier filter settings described above are used. DX then is an N5-P3 "peak-to-peak" estimate of P3. Theoretically, N5 may be an independent component in the ERP. DX serves as a criterion to ensure that late positive waves are P3's, not DC shifts.

Accordingly, the program has a direct P3 estimate (whether defined as MX or DX) for each of the 9 average ERP's within each channel. Preferably, only the PZ channel is utilized for diagnosis since it appears to be the most reliably diagnostic.

The procedures described herein, however, utilize only the direct P3 determinations with the output MX value for only the PZ site.

In the guilty knowledge procedure, the program computes the average MX for all 7 non-guilty items. This =MX$_i$. There is 1 guilty item, 1 to-be-counted (TBC) or to-be-"yes" (TBY) item and 7 non-guilty items. In developing a norm, it appears that a value of 9 computer units (which is about 3 μV, baseline to peak) is what the MX value will be determined for non-guilty items. For guilty items, P3 (baseline to peak) tends to be more than 19 units (or 6 μV). If the MX$i$ for non-guilty items is ≦9 units while the guilty item MX=MX$_g$ is greater than 19 units the printer prints "has guilty knowledge" with an appropriate probability statement. If the guilty MX value is greater than MX$_i$ by 10 units or more, a guilty diagnosis is output. It is noted on the basis of preliminary data that 9 is an average value for MX$_i$ with a standard error of about 4. If the MX$_g$ −MX$_i$ difference is within 4 units (i.e., if MXg≦13 given MXi=9) an "innocent" diagnosis is output. If the MXi versus MXg difference is greater than 4 but less than 10 units, an "indeterminate" diagnosis is output.

All the above assumes that 108 artifact-free trials were collected with no more than 54 trials rejected for artifact i.e., 162 trials (=150% of 108) were run in all. If this criterion is not met, i.e., if a 163rd trial is detected, the pogrom stops and reports this fact, noting that "Artifact Excess" was detected.

Further, DX must be less than 0, (which means the ERP does go negative after P3) in the guilty item average. Otherwise an apparent P3 could be a positive-going DC shift.

If the program detects MX values for less than 2 innocent items exceeding the value 19, "suspected non-cooperation; results indeterminate" is printed out. (This result suggests that the subject attempted to defeat the test by not following instructions, i.e., he was instructed to count only the TBC item but counted other items also. This could lead to P3 responses in control averages which can't happen otherwise. If the DX criterion is not met, "indeterminate" is output.

In control question procedures, all will have 1 or 2 relevant (r) items, 3 to 4 control (C) items, and 1-5 irrelevant (I) items. P3 will be determined in exactly the same way for the control question tests as it was in the guilty knowledge tests, for all, R, C, and I items. In order for the program to generate a guilty diagnosis, 6 conditions need to be satisfied:

---

(1) 108 artifact free trials in 162 attempts
(2) no evidence of non-cooperation or lack of following instructions by subject
(3) passing memory tests, post-trial As in guilty knowledge test (4) DX must be greater than 0.
(5) P3 average for R items must be less than 2 standard deviations larger than P3 for I item average.
(6) P3 average for R items must be a to-be-determined normative value larger than P3 average for C items. For an innocent diagnosis, one needs conditions (1)–(4) above satisfied and also
(5) P3 average for R items is within 1 standard deviation of P3 average for I items.
(5) P3 average for the C item is within 1 standard deviation of P3 average for R item (if the value for C is less than the value for R), or if the C value is less than the R value.

---

The program determines if the conditions listed above for control question tests are fulfilled, as in guilty knowledge procedure.

Although the present invention has been described with reference to preferred embodiments, workers skilled in the art will recognize that changes may be made in form and detail without departing from the spirit and scope of the invention.

What is claimed is:

1. A method of determining the cognitive response to personally meaningful information of a subject to a repeatedly presented significant guilty knowledge stimulus or stimuli interspersed with nonsignificant stimuli comprising:
   (a) providing a source of stipulation to the subject, including said guilty knowledge and said nonsignificant stimuli;
   (b) providing detection means for detecting event related potentials;
   (c) translating event related potentials to P300 brain waves;
   (d) obtaining P300 brain wave activity; and
   (e) analyzing said P300 brain wave activity for guilty knowledge detection.

2. The method of claim 1 wherein the event related potentials are detected, translated into P300 brain waves and analyzed by a computer.

3. A method of determining the cognitive response to personally meaningful information of a subject to a repeatedly presented significant control question stimulus or stimuli interspersed with non-significant stimuli comprising:
   (a) providing a source of stimulation to the subject, including said guilty knowledge and said nonsignificant stimuli;
   (b) providing detection means for detecting event related potentials;
   (c) translating event related potentials to P300 brain waves;
   (d) obtaining P300 brain have activity; and
   (e) analyzing said P300 brain wave activity for control question testing.

4. The method of claim 1 or 3 wherein the stimuli may be visual or auditory.

5. The method of claim 1 or 3 wherein the stimuli may be words.

* * * * *

UNITED STATES PATENT AND TRADEMARK OFFICE
CERTIFICATE OF CORRECTION

PATENT NO. : 4,932,416
DATED : June 12, 1990
INVENTOR(S) : Joel P. Rosenfeld

It is certified that error appears in the above-identified patent and that said Letters Patent is hereby corrected as shown below:

COLUMN 18

LINE 4
Claim 1, line 6, delete "stipulation" and insert --stimulation--;

LINE 30
Claim 3, line 13, delete "have" and insert --wave--.

Signed and Sealed this

Fifth Day of November, 1991

Attest:

HARRY F. MANBECK, JR.

*Attesting Officer*    *Commissioner of Patents and Trademarks*